(12) United States Patent
Gohil

(10) Patent No.: US 7,157,057 B2
(45) Date of Patent: Jan. 2, 2007

(54) APPARATUS FOR POSITIONING A WICK IN A DISPENSER FOR A VOLATILE LIQUID

(75) Inventor: Kishen Gohil, Surrey (GB)

(73) Assignee: Givaudan SA, Vernier (CH)

( * ) Notice: Subject to any disclaimer, the term of this patent is extended or adjusted under 35 U.S.C. 154(b) by 534 days.

(21) Appl. No.: 10/613,787

(22) Filed: Jul. 3, 2003

(65) Prior Publication Data

US 2005/0002834 A1    Jan. 6, 2005

(51) Int. Cl.
*A61L 2/00* (2006.01)

(52) U.S. Cl. .................. 422/123; 222/187; 239/44; 422/124

(58) Field of Classification Search ............... 422/123, 422/124; 239/44; 222/187
See application file for complete search history.

(56) References Cited

U.S. PATENT DOCUMENTS

| | | | |
|---|---|---|---|
| 1,962,100 A * | 6/1934 | Bryan ................ 239/44 |
| 2,246,008 A * | 6/1941 | Rooch ................ 239/42 |
| 2,616,759 A | 11/1952 | Walsh |
| 2,828,953 A | 4/1958 | Hartmann |
| 3,790,081 A | 2/1974 | Thornton et al. |
| 3,990,848 A | 11/1976 | Corris |
| 3,993,444 A | 11/1976 | Brown |
| 4,035,451 A | 7/1977 | Tringali |
| 4,166,087 A | 8/1979 | Cline et al. |
| 4,276,236 A | 6/1981 | Sullivan et al. |
| 4,294,778 A | 10/1981 | DeLuca |
| 4,323,193 A | 4/1982 | Compton et al. |
| 4,383,951 A | 5/1983 | Palson |
| 4,432,938 A | 2/1984 | Meetze, Jr. |
| 4,666,638 A | 5/1987 | Baker et al. |
| 4,695,435 A | 9/1987 | Spector |
| 4,707,338 A | 11/1987 | Spector |
| 4,739,928 A | 4/1988 | O'Neil |
| 4,743,406 A | 5/1988 | Steiner et al. |
| 4,857,240 A | 8/1989 | Kearnes et al. |
| 4,913,350 A * | 4/1990 | Purzycki ................ 239/44 |
| 4,931,224 A | 6/1990 | Holzner, Sr. |
| 5,000,383 A | 3/1991 | Van Der Heijden |
| RE33,864 E | 3/1992 | Steiner et al. |
| 5,114,625 A | 5/1992 | Gibson |

(Continued)

FOREIGN PATENT DOCUMENTS

DM    DM/054926    9/2000

(Continued)

OTHER PUBLICATIONS

International Search Report from the European Patent Office dated Sep. 30, 2004.

*Primary Examiner*—Krisanne Jastrzab
(74) *Attorney, Agent, or Firm*—Norris McLaughlin & Marcus, PA

(57) ABSTRACT

A wick for a dispenser for a volatile liquid which includes a body defining an opening in the body in which the opening is adapted to receive a member associated with the dispenser.

14 Claims, 2 Drawing Sheets

U.S. PATENT DOCUMENTS

| | | |
|---|---|---|
| 5,126,078 A | 6/1992 | Steiner et al. |
| 5,133,042 A | 7/1992 | Pelonis |
| 5,223,182 A | 6/1993 | Steiner et al. |
| 5,230,837 A * | 7/1993 | Babasade ............ 261/30 |
| 5,342,584 A | 8/1994 | Fritz et al. |
| 5,370,829 A | 12/1994 | Kunze |
| 5,376,338 A | 12/1994 | Zlotnik |
| 5,547,616 A | 8/1996 | Dancs et al. |
| 5,647,053 A | 7/1997 | Schroeder et al. |
| 5,662,835 A | 9/1997 | Collingwood |
| D386,974 S | 12/1997 | Wefler |
| D393,063 S | 3/1998 | Wefler |
| 5,909,845 A | 6/1999 | Greatbatch et al. |
| 5,970,643 A | 10/1999 | Gawel, Jr. |
| 6,371,450 B1 | 4/2002 | Davis et al. |
| 6,555,068 B1 | 4/2003 | Smith |
| 2003/0146292 A1 | 8/2003 | Schramm et al. |
| 2004/0182949 A1* | 9/2004 | Duston et al. ............ 239/44 |

FOREIGN PATENT DOCUMENTS

| | | |
|---|---|---|
| EP | 1 283 062 | 12/2003 |
| GB | 2 194 148 A | 3/1988 |
| WO | WO 95/10352 | 4/1995 |
| WO | WO 01/02025 A1 | 1/2001 |
| WO | WO 01/23008 | 4/2001 |
| WO | WO 02/30220 A1 | 4/2002 |
| WO | WO 02/31413 A2 | 4/2002 |

* cited by examiner

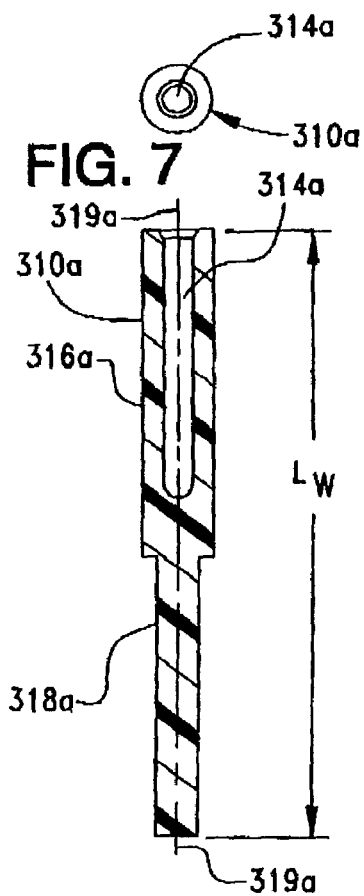
FIG. 7
FIG. 6
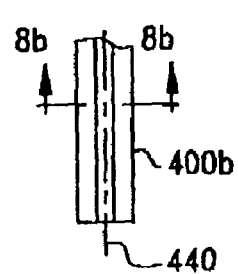
FIG. 8a
FIG. 8b
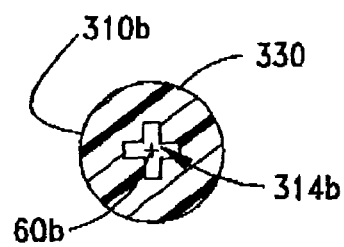
FIG. 9b
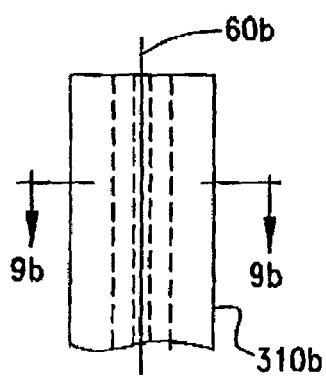
FIG. 9a
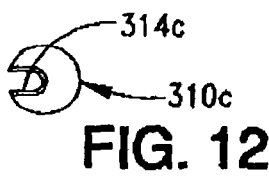
FIG. 12
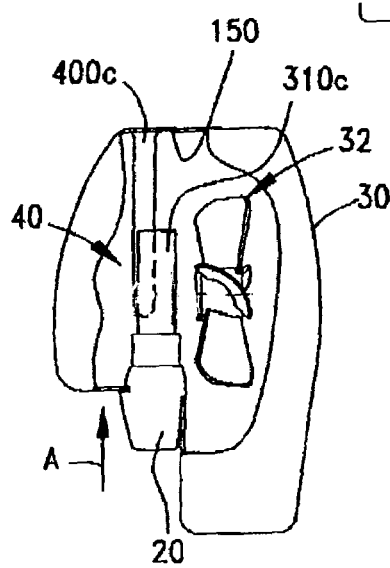
FIG. 10
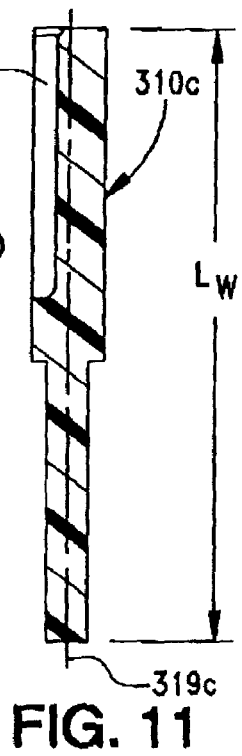
FIG. 11
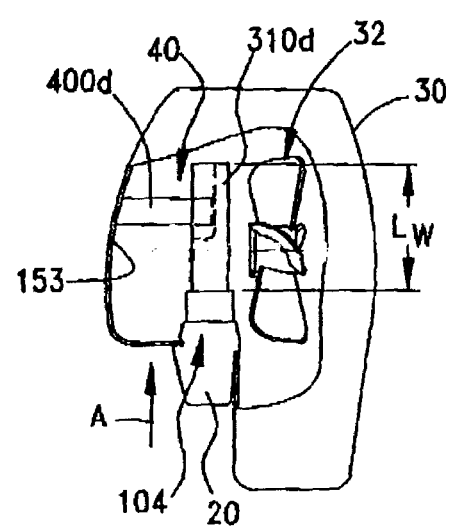
FIG. 13

APPARATUS FOR POSITIONING A WICK IN A DISPENSER FOR A VOLATILE LIQUID

FIELD OF THE INVENTION

The present invention relates to a dispensing system for volatile liquids and, more particularly, to wick-based dispensers for a volatile liquid.

BRIEF DESCRIPTION OF THE DRAWINGS

FIG. 6 is an enlarged cross-sectional view of the wick of the present invention taken along a length of the wick;

FIG. 7 is a top view of the wick of FIG. 6;

FIG. 8a partial side view of a second embodiment of the member of the present invention;

FIG. 8b is the cross-sectional view of the second embodiment member taken along line 8b—8b of FIG. 8a;

FIG. 9a is a partial side view of a second embodiment of the wick of the present invention;

FIG. 9b is the cross-sectional view of the second embodiment of the wick taken along line 9b—9b of FIG. 9a;

FIG. 10 is a side partial cutaway view of a third embodiment of the wick and engaged with a member of the present invention;

FIG. 11 is an enlarged cross-sectional view of the third embodiment of the wick taken along a length of the wick shown in FIG. 10;

FIG. 12 is a top view of the third embodiment of the wick of FIG. 11; and

FIG. 13 is a side partial cutaway view of the dispenser housing showing a fourth embodiment of the present invention.

DETAILED DESCRIPTION OF THE INVENTION

Figure 1:
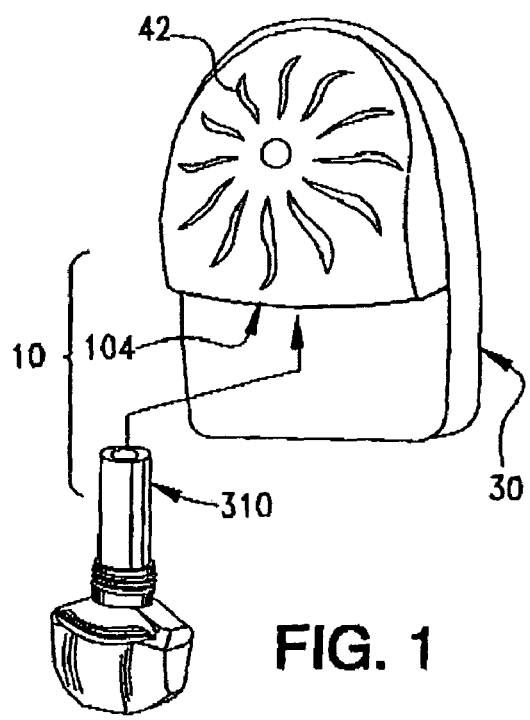
FIG. 1 is a perspective view of the dispenser showing insertion of a wick of the present invention into the housing of the dispenser.
Figure 2:
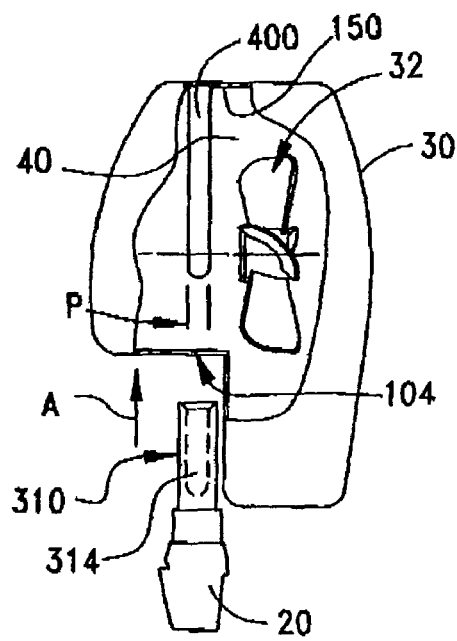
FIG. 2 is a side partial cutaway exploded view of FIG. 1 showing insertion of the wick of the present invention.

Referring to FIGS. 1 and 2, according to the present invention, a volatile liquid dispenser 10 includes a housing 30, a motorized fan 32 mounted in housing 30 for generating an air stream and a wick, generally designated 310, coupled to housing 30. Wick 310 may be formed from a plastic material such as nylon, or in particular ultra high molecular weight, high density polyethylene (HDPE). Portions of housing 30 may form an enclosure 40 for fan 32 and for receiving wick 310 into the air stream generated by fan 32. Liquid dispenser 10 is designed to disseminate a volatile liquid, such as a fragrance compound, into a room. The fragrance compound is disseminated from openings 42 (FIG. 1) in housing 30 via a forced air stream flowing around wick 310 at room ambient temperature.

It is desired to position and secure an appropriate wick 310 in enclosure 40 formed by housing 30 so as to be in alignment with fan 32. Wick 310 may be secured in a desired position by coupling the wick to dispenser housing 30 using any one of numerous methods. An example suitable for coupling wick 310 to housing 30 is shown in FIGS. 2 and 3.

Figure 5:
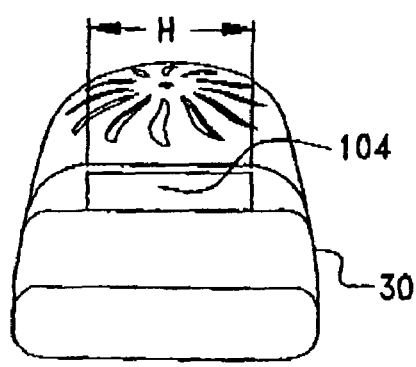
FIG. 5 is a bottom view of the dispenser housing of FIG. 1 showing an opening into an enclosure formed by the housing.

In turn, wick 310 is secured in a container 20. As can be seen in FIGS. 2, 3 and 5, container or reservoir 20 for holding the volatile liquid has ridges integral in opposing sidewalls that engage corresponding opposing sidewalls of housing opening 104. A portion of wick 310 resides inside container 20 and is in contact with the volatile liquid. Another portion of wick 310 extends outside container 20, and is positioned in alignment with fan 32 with wick 310 inserted into housing 30. When positioned in alignment with fan 32, the exposed portion of wick 310 is immersed in the air stream generated by fan 32 with the fan in operation. The volatile liquid migrates along wick 310 from volatile liquid reservoir 20 to a portion of wick 310 immersed in the air stream generated by fan 32, where it is evaporated from the surface of wick 310 by the air stream and moved out of housing 30 through openings 42, shown in FIG. 1.

In order to ensure effective dissemination of the fragrance compound, it is desirable that the wick be positioned and secured in alignment with fan 32 so as to enable air flow over as much of the external surface of wick 310 as possible. A positioning system is provided to facilitate alignment between wick 310 and fan 32 when wick 310 is inserted into housing 30 through opening 104, as shown in FIGS. 1–5. In referring to FIG. 1, the positioning system of the present invention generally comprises an alignment member 400 in association with housing 30, and an opening 314 formed in wick 310 configured to receive a portion of alignment member 400 therein, as seen in FIG. 2.

Figure 3:
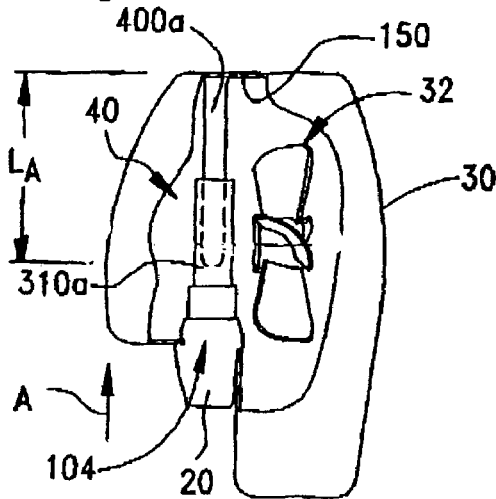
FIG. 3 is an assembled view of the present invention of FIG. 2.
Figure 4:
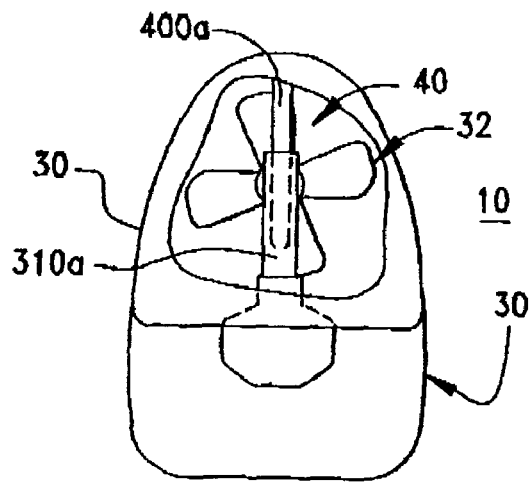
FIG. 4 is a front schematic view of the dispenser of FIG. 1 showing the dispenser housing partially cut away with the wick positioned in the housing with the member inserted within the wick.

Referring to FIGS. 3, 4, 6 and 7, a first embodiment of the positioning system of the present invention is shown. Alignment member 400a is generally cylindrical. Alignment member 400a is affixed to a surface 150 of the interior of housing 30 opposite housing opening 104, as seen in FIGS. 2 and 3 and extends into alignment with fan 32 mounted in dispenser housing 30, as seen in FIG. 4.

Alignment member 400a is positioned such that, when engaged with wick 310a, member 400a positions and secures wick 310a in alignment with fan 32 in a manner to be described below. In this embodiment, alignment member 400a has a length $L_A$ (FIG. 3) and extends from surface 150 generally toward housing opening 104. Length $L_A$ may be specified such that alignment member 400a extends to a point proximate housing opening 104.

Referring to FIGS. 6 and 7, wick 310a has an elongate body defining an opening 314a. Opening 314a is formed in a top portion 316a of wick 310a, and extends along a length $L_W$ and in the present example includes a longitudinal axis 319a. Wick opening 314a is sized to receive at least a portion of alignment member 400a therein when wick 310a is inserted into housing 30. In this embodiment, wick opening 314a comprises a hole extending from top portion 316a of wick 310a toward a bottom portion 318a of wick 310a.

As seen in FIGS. 1–4 and 6, as wick 310a is inserted into housing 30 through opening 104, alignment member 400a engages wick opening 314a, which is positioned in this example in the top of wick 310a, in a direction generally aligned with a length $L_W$ (FIG. 6) of wick 310a and is received in wick opening 314a. Engagement between alignment member 310a and wick opening 314a aligns wick 310a with fan 32 and secures the wick in alignment with the fan.

Referring to FIGS. 2 and 5, alignment member 400a has a width dimension P defined with respect to housing opening dimension H by the relationship P < H. In the example shown, both alignment member 400a and wick opening 314a are substantially cylindrical. However, the principles described below with regard to this embodiment may also be applied to non-cylindrical alignment members and wick openings. Wick openings may be regular or irregular in shape.

Referring to FIG. 2, dimension P of alignment member 400 is defined by a width or diameter of alignment member 400a. Opening dimension H in housing 30 is sized to admit wick 310a. Member 400 extends in interior 40 of housing 30 from interior surface 150 toward opening 104. As wick 310a is inserted into housing 30 through opening 104, alignment member 400a engages wick opening 314a in a direction aligned with wick length 319a and is received in wick opening 314a.

The dimension H of opening 104 restricts the dimension of wick 310a being inserted into housing 30. Member 400a having a particular shape and size will further qualify the wick to be inserted into housing 30, thereby requiring a wick 400a that has an opening 314a which is compatible with member 400a for insertion.

Thus, in the present invention the wick 400a must clear dimension H of opening 104 and have an opening 314a which is compatible with member 400a for insertion thereby assuring reliable alignment and properly configured wicks for the subject dispenser.

Opening 314a of wick 310a has generally a slightly larger dimension than the corresponding member 400a to facilitate insertion of member 400a into opening 314a.

Referring to FIGS. 8a, 8b and 9a and 9b, second embodiments of member 400b and wick 310b are shown. Opening 314b in wick 310b has a shape that is congruent with the shape of alignment member 400b as seen in FIGS. 8b and 9b. That is, a perimeter 330 of a cross section of wick opening 314b taken transverse to longitudinal axis 60b of wick 310b has a shape corresponding to the shape of a perimeter 430 of a cross section of alignment member 400b taken transverse to longitudinal axis 440 of alignment member 400b. This arrangement provides proper alignment of the wick with the fan and can restrict the insertion of certain wicks into the housing. That is, if the shape and size of perimeter 430 of the alignment member 400b cross section is incompatible with the shape and size of perimeter 330 of wick 310b opening cross section, wick opening 314b may not be able to receive alignment member 400b when wick 310b is attempted to be inserted into housing 30.

Referring to FIGS. 10–12, a third embodiment of wick 310c is shown. Wick opening 314c comprises a slot 314c formed on an outer surface or side of wick 310c and extends along a side of wick 310c. In this embodiment, alignment member 400c is generally longitudinal and is affixed to surface 150 of housing 30 opposite housing opening 104. As wick 310c is inserted into housing 30 through opening 104, alignment member 400c engages slot 314c in a direction generally along a length $L_w$ and is received in slot 314c.

Referring to FIG. 13, in a fourth embodiment of the present invention, alignment member 400d extends from a surface 153 of housing 30 positioned generally transverse to a direction of insertion "A" of wick 310d into housing opening 104. Alignment member 400d extends from surface 153 in a direction generally transverse to the direction of insertion of wick 310d. As wick 310d is inserted into housing 30 through opening 104, alignment member 400d engages slot 314d in a direction generally transverse to wick length $L_w$, as shown in FIG. 13, and is received in slot 314d.

As discussed earlier, the wicks can be constructed of various materials and in particular (HDPE). In the example shown, the wick is constructed of a smaller diameter lower wick segment which generally has small pore sizes than the larger diametered top portion of the wick. The larger diametered top portion is generally cylindrical and caps and surrounds a top portion of the smaller diametered lower segment of the wick. The ratio of difference in pore sizes is above two and even more preferable, above ten. The pore size, for example, in the lower smaller diametered portion of the wick is less than one micron and the larger diametered upper portion has pore sizes of around 10 micron.

It is also desirable to utilize wicks which have cross sectional perimeters taken transverse to the length of the wick which a simple geometric shape including shapes which readily permit air flow about the surface and create little, if any, turbulence thereby promoting efficiency of the air stream in evaporating the volatile liquid positioned on the surface of the wick.

INDUSTRIAL APPLICABILITY

The present invention provides a keying system for positioning and securing a wick in alignment with a fan mounted in a housing of a volatile liquid dispenser. This helps ensure that proper positioning of the wick within an air stream generated by the fan is maintained. The present invention also provides a way for the wicks insertable into the housing.

It should be understood that the preceding is merely a detailed description of various embodiments of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

The invention claimed is:

1. A dispenser for dispensing volatile liquid with a wick, the dispenser comprising
   a housing including a wick alignment member having a top end and a bottom end,
   a container including volatile liquid,
   the wick having two portions, the first portion extending into the container including volatile liquid and the second portion extending away from the container and into the housing, and wherein the second portion comprises an opening adapted for alignment the wick receiving member.

2. The dispenser wick of claim 1 wherein the opening in the second portion of the wick and the alignment member are substantially coaxially mounted.

3. The dispenser of claim 1, wherein the opening in the second portion of the wick and the alignment member are substantially perpendicularly mounted.

4. The dispenser of claim 1, wherein the opening in the second portion is formed congruent with a shape of the alignment member.

5. The dispenser of claim 1, wherein the opening in the second portion of the wick is larger than the alignment member.

6. The dispenser of claim 2, wherein the alignment member is elongated and wherein the opening in the second portion has a depth to accommodate the elongated alignment member.

7. The dispenser of claim 3, wherein the opening in the second portion of the wick extends along the side of the second portion and wherein the alignment member is elongated.

8. The dispenser of claim 1, wherein the housing comprises an opening adapted to removably receive and retain the container holding the volatile liquid and including the wick, through and wherein the opening has a width H and the alignment member has a width P, and wherein P is less than H.

9. The dispenser of claim 8, wherein the alignment member is affixed to an interior surface of the housing, opposite the housing opening.

10. The dispenser of claim 3, wherein the alignment member is affixed to an interior surface of the housing, substantially perpendicular to the second portion of the wick.

11. The dispenser wick of claim 1, wherein the alignment member has a geometric cross-section.

12. The dispenser of claim 1, wherein the housing further comprising a fan, the fan being arranged in the housing such that the fan aligns with the second portion of the wick.

13. The dispenser of claim 12, wherein the container is removably mounted in the housing.

14. A wick for a dispenser for volatile liquid, comprising:

a container containing volatile liquid, a wick having two portions, a first portion extending into the liquid in the reservoir and a second portion extending outside the container, and a housing holding the container securely, the housing additionally comprising an alignment member which fits into an opening in the second portion of the wick when the wick is correctly positioned for the dispensing of liquid.

* * * * *

UNITED STATES PATENT AND TRADEMARK OFFICE
CERTIFICATE OF CORRECTION

PATENT NO. : 7,157,057 B2
APPLICATION NO. : 10/613787
DATED : January 2, 2007
INVENTOR(S) : Gohil Page 1 of 1

It is certified that error appears in the above-identified patent and that said Letters Patent is hereby corrected as shown below:

Column 4, Line 52, "The dispenser wick of claim 1" should read -- The dispenser of claim 1, --

Column 5, Line 18, "The dispenser wick" should read -- The dispenser --

Signed and Sealed this

Third Day of April, 2007

JON W. DUDAS
*Director of the United States Patent and Trademark Office*